US006828127B2

(12) United States Patent
Cheynet-Sauvion et al.

(10) Patent No.: US 6,828,127 B2
(45) Date of Patent: Dec. 7, 2004

(54) METHOD OF AMPLIFYING AN RNA TARGET SEQUENCE USING AN RNA POLYMERASE FUNCTIONING PREFERABLY ON RNA TEMPLATE

(75) Inventors: Valérie Cheynet-Sauvion, Verin (FR); Nadége Arnaud-Barbe, Saint Sorlin (FR); Guy Oriol, Saint Chamond (FR); William T. McAllister, Perth Amboy, NJ (US); Bernard Mandrand, Villeurbanne (FR); François Mallet, Villeurbanne (FR)

(73) Assignee: Bio Merieux, Marcy l'Etoile (FR)

( * ) Notice: Subject to any disclaimer, the term of this patent is extended or adjusted under 35 U.S.C. 154(b) by 0 days.

(21) Appl. No.: 09/402,131

(22) PCT Filed: Mar. 27, 1998

(86) PCT No.: PCT/FR98/00635

§ 371 (c)(1),
(2), (4) Date: Dec. 8, 1999

(87) PCT Pub. No.: WO98/45449

PCT Pub. Date: Oct. 15, 1998

(65) Prior Publication Data

US 2002/0119449 A1 Aug. 29, 2002

(30) Foreign Application Priority Data

Apr. 4, 1997 (FR) ............................................. 97 04166

(51) Int. Cl.[7] ............................ C12P 13/34; C12Q 1/68; C07H 21/04
(52) U.S. Cl. ........................ 435/91.21; 435/6; 435/91.1; 435/91.3; 435/183; 536/23.1; 536/24.33; 536/25.3
(58) Field of Search .......................... 435/6, 91.1, 91.2, 435/183, 91.21, 91.3, 5, 91.51; 436/94; 536/23.1, 24.3, 24.33, 25.3

(56) References Cited

U.S. PATENT DOCUMENTS 5,891,681 A  4/1999  Mallet et al.

FOREIGN PATENT DOCUMENTS

| DE | 0 659 881 A1 | 6/1995 |
| EP | 0 747 488 A1 | 12/1996 |
| FR | 2 714 062 | 6/1995 |
| WO | WO 90/06376 | 6/1990 |
| WO | WO 95/03426 | 2/1995 |
| WO | WO 97/12033 | 4/1997 |

OTHER PUBLICATIONS

R. Sousa et al., *A Mutant T7 RNA Polymerase as a DNA Polymerase*, EMBO Journal, vol. 14, No. 18, pp. 4609–4621 (1995).
W. McAllister, *Structure and Function of the Bacteriophage T7 RNA Polymerase (or, the Virtues of Simplicity)*, Cellular and Molecular Biology Research, vol. 39, pp. 385–391 (1993).
C.A. Raskin et al., *Substitution of a Single Bacteriophage T3 Residue in Bacteriophage T7 RNA Polymerase at Position 748 Results in a Switch in Promoter Specificity*, J. Mol. Biol. 228, pp. 506–515 (1992).
C. Cazenave et al., *RNA Template–Directed RNA Synthesis by T7 RNA Polymerase*, Proc. Natl. Acad. Sci. USA, vol. 91, pp. 6972–6976 (1994).
R. Sousa, *Structural and Mechanistic Relationships Between Nucleic Acid Polymerases*, TIBS 21, pp. 186–190 (1996).
S.L. Stahl et al., *Nucleotide Sequence of the Cloned Gene for Bacteriophage T7 RNA Polymerase*, J. Mol. Biol. 148, pp. 481–485 (1981).
B. van Gemen et al., *Qualitative and Quantitative Detection of HIV–1 RNA by Nucleic Acid Sequence–Based Amplification*, Aids 7 (suppl 2), pp. S107–S110 (1993).
Leary et al., "DNA–dependent RNA polymerase from bacteriophage T3 transcribes and amplifies and RNA template in vitro," *Gene*, vol. 106, 1991, pp. 93–96.
Pfeifer et al., "Detection of DNA adducts at the DNA sequence level by ligation–mediated PCR," *Mutat. Res.*, vol. 288, No. 1, 1993, pp. 39–46.
Chamberlin et al., "Characterization of T7–specific Ribonucleic Acid Polymerase," *The Journal of Biological Chemistry* vol. 248, No. 6, 1973, pp. 2235–2244.
Konarska et al., "Replication of RNA by the DNA–Dependent RNA Polymerase of Phage T7," *Cell*, vol. 57, 1989, pp. 423–431.
Konarska et al., "Structure of RNAs Replicated by the DNA–Dependent T7 RNA Polymerase," *Cell*, vol. 63, 1990, pp. 609–618.
Daube et al., "RNA Displacement Pathways during Transcription from synthetic RNA–DNA Bubble Duplexes," *Biochemistry*, vol. 33, 1994, pp. 340–347.
McAllister et al., "The phage RNA polymerases are related to DNA polymerases and reverse transcriptases," *Molecular Microbiology*, vol. 10, No. 1, 1993, pp. 1–6.

(List continued on next page.)

*Primary Examiner*—Bradley L. Sisson
(74) *Attorney, Agent, or Firm*—Oliff & Berridge,PLC

(57) ABSTRACT

Disclosed is a process for transcribing RNA using a nucleotide reagent as the promoter. Such a reagent enables any type of RNA to be transcribed without sequence specification and without protein cofactors, by means of an RNA polymerase that is known to be DNA-dependent such as the RNA polymerase of the phage T7, or by means of new, mutated RNA polymerase with the ability to synthesize a transcription product of a polynucleotide matrix with a higher yield when the matrix is RNA than when said matrix is DNA. This type of RNA polymerase can be obtained by effecting mutations on a coding gene for a wild-type RNA polymerase, and then by selecting the mutated RNA polymerase with said ability. The invention can be applied notably to the detection, synthesis or quantification of RNA.

17 Claims, 6 Drawing Sheets

OTHER PUBLICATIONS

Figure 1A:
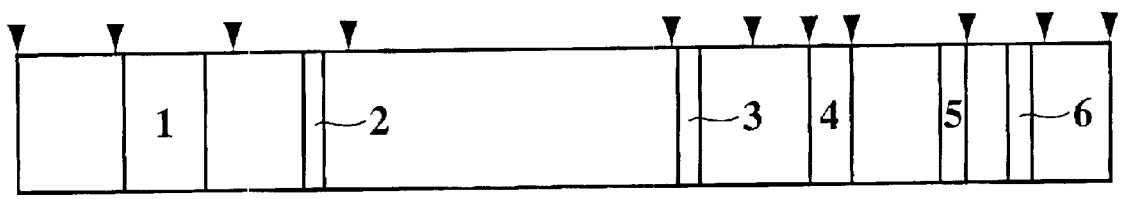

Moras, "Two sisters and their cousin," *Nature*, vol. 364, 1993, pp. 572–573.

Delarue et al., "An attempt to unify the structure of polymerases," *Protein Engineering*, vol. 3, No. 6, 1990, pp. 461–467.

Poch et al., "Identification of four conserved motifs among the RNA–dependent polymerase encoding elements," *The EMBO Journal*, vol. 8, No. 12, 1989, pp. 3867–3874.

Sousa et al., "Crystal structure of bacteriophage T7 RNA polymerase at 3.3 Å resolution," *Nature*, vol. 364, 1993, pp. 593–598.

Joho et al., "Identification of a Region of the Bacteriophage T3 and T7 RNA Polymerases that Determines Promoter Specificity," *J. Mol. Biol.*, vol. 215, 1990, pp. 31–39.

Moffatt et al., "Nucleotide Sequence of the Gene for Bacteriophage T7 RNA Polymerase," *J. Mol. Biol.*, vol. 173, 1984, pp. 265–269.

SEQUENCE LISTING

<160> NUMBER OF SEQ ID NOS: 13

<210> SEQ ID NO 1
<211> LENGTH: 49
<212> TYPE: DNA
<213> ORGANISM: Artificial Sequence
<220> FEATURE:
<223> OTHER INFORMATION: Description of Artificial Sequence:
      Transcription Template

<400> SEQUENCE: 1
tgtacttgga gcgttatgct gctagatctc cctatagtga gtcgtatta          49

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence:
      Transcription Template

<400> SEQUENCE: 2
gccataacca tgagtgaaca ctgcggccaa ccctatagtg agtcgtatta          50

<210> SEQ ID NO 3
<211> LENGTH: 49

```
<212> TYPE: DNA
<213> ORGANISM: Artificial Sequence
<220> FEATURE:
<223> OTHER INFORMATION: Description of Artificial Sequence:
      Transcription Template

<400> SEQUENCE: 3
tgtacttgga gcgttatgct gctagacaac cctatagtga gtcgtatta          49

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence:  Probe

<400> SEQUENCE: 4
tgtacttgga gcgtta                                              16

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence:  Probe

<400> SEQUENCE: 5
gccataacca tgagtg                                              16

<210> SEQ ID NO 6
<211> LENGTH: 28
<212> TYPE: PRT
<213> ORGANISM: Escherichia coli

<400> SEQUENCE: 6

Val Thr Arg Ser Val Thr Lys Arg Ser Val Met Thr Leu Ala Tyr Gly
 1               5                  10                  15

Ser Lys Glu Phe Gly Phe Arg Gln Gln Val Leu Asp
            20                  25

<210> SEQ ID NO 7
<211> LENGTH: 25
<212> TYPE: PRT
<213> ORGANISM: Hepatitis C Virus

<400> SEQUENCE: 7

Asn Cys Gly Tyr Arg Arg Cys Arg Ala Ser Gly Val Leu Thr Thr Ser
 1               5                  10                  15

Cys Gly Asn Thr Leu Thr Cys Tyr Ile
            20                  25

<210> SEQ ID NO 8
<211> LENGTH: 25
<212> TYPE: PRT
<213> ORGANISM: Yeast Integrase

<400> SEQUENCE: 8

His Asn Thr Thr Leu Gly Ile Pro Gln Gly Ser Val Val Ser Pro Ile
 1               5                  10                  15

Leu Cys Asn Ile Phe Leu Asp Lys Leu
            20                  25

<210> SEQ ID NO 9
<211> LENGTH: 10
```

-continued

```
<212> TYPE: PRT
<213> ORGANISM: Artificial Sequence
<220> FEATURE:
<223> OTHER INFORMATION: Description of Artificial Sequence:  Antigen
      of a Mouse Monoclonal Antibody

<400> SEQUENCE: 9

Met Arg Gly Ser His His His His His
  1               5                 10

1
<210> SEQ ID NO 10
<211> LENGTH: 13
<212> TYPE: PRT
<213> ORGANISM: Unknown Organism
<220> FEATURE:
<223> OTHER INFORMATION: Description of Unknown Organism: Poly-histidine
      Tail

<400> SEQUENCE: 10

Met Arg Gly Ser His His His His His Ser Val Leu Glu
  1               5                   10

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence:
      Non-template Promoter Strand

<400> SEQUENCE: 11
taatacgact cactatag                                             18

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence:
      Non-template Strand

<400> SEQUENCE: 12
taatacgact cactataggg ttggccgcag tgttcactca tggttatggc           50

<210> SEQ ID NO 13
<211> LENGTH: 50
<212> TYPE: DNA
<213> ORGANISM: Artificial Sequence
<220> FEATURE:
<223> OTHER INFORMATION: Description of Artificial Sequence:
      Transcription Template

<400> SEQUENCE: 13
gccauaacca ugagugaaca cugcggccaa ccctatagtg agtcgtatta           50
```

METHOD OF AMPLIFYING AN RNA TARGET SEQUENCE USING AN RNA POLYMERASE FUNCTIONING PREFERABLY ON RNA TEMPLATE

The subject of the invention is a method of transcription, which makes it possible to synthesize RNA strands complementary to an RNA template, as well as new RNA polymerases which make it possible to carry out this method.

The method of the invention leads to the amplification of RNA present in small quantities in a biological sample, and thus allows the detection and/or quantification of the RNA in the sample, or the sequencing of the product of amplification, in particular in the field of microbiology and virology, and more generally in the field of medical diagnosis. The method of the invention may also be used in the synthesis of RNA probes.

It is known that in microbiology and in virology, the microorganisms which it is sought to identify are often viable bacteria (therefore containing more RNA than DNA) or RNA viruses such as the HIV and HCV viruses. It is also known that in various pathologies, it is often advantageous to monitor the variations in the expression of genes, and therefore in the synthesis of messenger RNA.

It is therefore important to be able to have a simple and effective method of amplifying an RNA target.

The PCR method, which makes it possible to cyclically amplify a DNA target, uses a single enzyme but requires the production of temperature cycles, generally at three different temperatures. The PCR method may be adapted to the amplification of an RNA target by adding an additional enzymatic activity of RNA-dependent DNA polymerase, which further complicates this method.

The so-called NASBA/TMA method of amplification has the advantage of being an isothermic method, but requires the use of three enzymatic activities (RNA-dependent DNA polymerase, RNase H and DNA-dependent RNA polymerase) carried by two or three enzymes.

It is therefore desirable to be able to have a simple and automatable method of amplification of RNA, and in particular an isothermic method using only one enzyme.

To avoid the disadvantages, which have just been mentioned, of known amplification techniques, it therefore appears to be necessary to use, for the amplification of RNA, an RNA-dependent RNA polymerase activity.

Unfortunately, the known natural RNA-dependent RNA polymerases (RNAd RNAp) are not suitable for such a use because they have specific requirements as regards the RNA template, and their activity requires the presence of protein cofactors (also called auxiliary protein factors or associated protein factors).

It has now been discovered that some known DNA-dependent RNA polymerases are capable of transcribing a single-stranded RNA in the presence of a double-stranded DNA promoter. Furthermore, some of these enzymes, which are transformed by mutation, are capable of synthesizing a transcriptional product with a better yield when the template consists of RNA than when the template consists of DNA.

In the present application, the term "transcription" designates the synthesis of several strands of RNA in the presence of a polynucleotide template and of ribonucleoside triphosphates, in an appropriate reaction medium and under conditions allowing the catalytic activity of an RNA polymerase to be exerted. The transcription occurs by synthesis of a complementary or antiparallel copy of the template. The strand of the template which is copied is called the transcribed strand or the template strand. The synthesis of the RNA progresses in the 5'-3' direction.

It is known that some RNA polymerases function under the control of a promoter. A promoter is a double-stranded nucleotide sequence recognized for the RNA polymerase and necessary for the initiation of transcription.

It should be recalled that when the template strand is linked to the promoter, the first nucleotide transcribed on the template strand, linked by its 3' end to the 5' end of one of the strands of the promoter, is designated by +1. The strand of the promoter which is linked to the template strand is called the antisense strand. The other strand of the promoter, which is complementary to the antisense strand, and hybridized to it, is called sense strand. The successive nucleotides which are situated on the side of the promoter, with respect to nucleotide +1, are, starting from +1, numbered −1, −2, −3, and the like.

The position −1 therefore corresponds to the 5' end of the antisense strand of the promoter, and to the 3' end of the sense strand. However, some authors include the nucleotide sequence corresponding to the region where the transcription starts (in particular the sequence from +1 to +6, for which a consensus sequence can generally be defined) in the definition of the sequence of the promoter.

On the template strand, the positions of the successive nucleotides copied, starting from +1, and therefore in the 3'-5' direction, are noted +2, +3, and the like.

In the text which follows, the terms sense strand and antisense strand are generally used for the promoter itself (positions numbered negatively), and the term non-template strand is used for any strand linked to the 3' end of the sense strand, and the term template strand for any strand linked to the 5' end of the antisense strand or for any strand hybridized to the non-template strand. In a given polynucleotide strand, "upstream region" refers to a region situated on the side of the 5' end, and "downstream region" a region situated on the side of the 3' end. However, in the domain of transcription under the control of a promoter, and without taking into consideration a particular strand, "upstream" region traditionally refers to the region which, relative to position +1, is on the side of the promoter (positions indicated by negative numbers), and "downstream" region the region situated on the side of the template copied (positions indicated by positive numbers), such that the downstream direction then corresponds to the 3'-5' direction on the template strand, and to the 5'-3' direction on the newly-synthesized RNA strand.

The template strand is not necessarily linked to the 5' end of the antisense strand of the promoter. However, it should, in this case, be hybridized to a complementary and antiparallel strand (non-template strand) which is itself linked by its 5' end to the 3' and of the sense strand of the promoter; see ZHOU W. and DOETSCH P. W., Biochemistry 33, 14926–14934 (1994) and ZHOU W. et al., Cell 82, 577–585 (1995). In such a case, the transcription may start in any position, which may range from +1 to +24, corresponding to the 3' end of the template strand or of the part of the template strand hybridized with the non-template strand.

Compared with bacterial, eukaryotic or mitochondrial RNA polymerases, the phage RNA polymerases are very simple enzymes. The best known among them are the RNA polymerases of the T7, T3 and SP6 bacteriophages. The bacteriophage RNA polymerase has been cloned; see in particular U.S. Pat. No. 4,952,496. These enzymes are highly homologous to one another and consist of a single subunit. The natural promoters specific for the RNA polymerases of the T7, T3 and SP6 phages are well known. The sequencing of the whole genome of the bacteriophage T7 (Dunn et al., J. Mol. Biol. 166, 477–535 (1983)) has made it possible to define the existence of 17 promoters on the DNA of this phage. Comparison of these 17 sequences shows that 23 contiguous nucleotides situated between positions −17 and +6 relative to the site of initiation (position +1) of transcription, are highly conserved. These nucleotides are even identical in five so-called class III promoters, which are the most efficient in particular in vitro. Likewise, many promoter sequences specific for the T3 RNA polymerase also exhibit a very high homology, in particular between positions −17 and +6. Moreover, several different sequences of promoter for phage SP6 RNA polymerase have been identified and also exhibit a high homology; see Brown J. E., et al., *Nucleic Acids Res.* 14, 3521–3526 (1986).

It is therefore possible to consider that the various phage RNA polymerases mentioned above form part of a family of RNA polymerases which recognize promoters having a consensus sequence from position −17 to position +6, and in particular from position −17 to position −1.

The method of the invention makes it possible to transcribe any RNA sequence because the RNA polymerases, capable of transcribing RNA under the control of a promoter, which are described in the present application, may transcribe RNA without a high sequence specificity. It is known, nevertheless, that some sequences for initiation of transcription, in particular from position +1 to position +6, are more favorable than others for obtaining transcripts of the expected length with a given phage RNA polymerase, in the case of the transcription of DNA; see for example Milligan J. F. et al., *Nucleic Acids Research*, 15, 8783–8798 (1987). The RNA polymerases capable of transcribing RNA which are described in the present application may also function with variable yields according to the sequence of the region for initiation of transcription. The sequences which are most suitable for a given RNA polymerase may be determined, where appropriate, by simple routine experiments similar to those described by Milligan et al. in the article which has just been mentioned. In addition, as will be seen below, the method of transcription of the invention makes it possible, where appropriate, either to start the transcription in a favorable region of the RNA to be transcribed, or to provide a reagent-promoter which already contains a region for initiation of transcription having a sequence favorable for a given RNA polymerase.

The subject of the present invention is therefore a method of amplifying any RNA target sequence, by transcription under the control of a promoter, in an RNA sample comprising said target sequence, in which said sample is brought into contact:

with a reagent capable of hybridizing with said RNA comprising said target sequence, and with an enzymatic system comprising an RNA-dependent RNA polymerase activity, under conditions allowing the hybridization of said reagent with said RNA comprising said target sequence and under conditions allowing the functioning of said RNA-dependent RNA polymerase activity; in which said reagent contains:

(i) a first nucleotide strand comprising: a) a first nucleotide segment capable of playing the role of sense strand of a promoter for said RNA polymerase activity and b), downstream of said first segment, a second nucleotide segment comprising a sequence capable of hybridizing with a region of said RNA, and (ii) in the hybridized state on the first strand, a second nucleotide strand comprising a third nucleotide segment capable of hybridizing with said first segment so as to form with it a functional double-stranded promoter;

and in which said RNA polymerase activity is capable of transcribing an RNA template, in the presence of said reagent hybridized with said template, in the absence of associated protein factor and in the absence of a ligase activity.

The general conditions allowing the hybridization of nucleotide strands are known, and specific conditions may be easily determined, by routine experiments, for strands of a given sequence. The conditions allowing the functioning of the RNA polymerase activity, in the presence of ribonucleoside triphosphates, may also be easily determined by experiments, optionally with the aid of the information provided in the experimental section below.

The 3' end of the first segment corresponds to position −1 in the transcriptional system used. The first segment contains a sufficient number of nucleotides to be able, in the hybridized state, to play the role of a promoter for an RNA polymerase. According to a specific embodiment, the first segment contains at least 9 nucleotides.

In patent FR 2,714,062, it has been shown that short sequences of 6 to 9 consecutive nucleotides chosen from the −12 to −4 region of the sense strand of a promoter for a phage RNA polymerase are capable of playing the role of functional promoters in the transcription of a DNA target sequence.

The reagent used in the method of the invention may also exhibit at least one of the following characteristics:

said third segment is flanked, at its upstream end, by a fourth nucleotide segment which is shorter than said second segment of the first strand;

said fourth segment is capable of hybridizing with a portion opposite said second segment.

said first and third segments consist of DNA;

said third and fourth segments consist of DNA or RNA.

The third segment may have the same length as the first segment. It may also be shorter or longer, but its 5' end must correspond to position −1 (that is to say the position immediately preceding the position for initiation of transcription in the case where the template strand is linked to the promoter), when it is hybridized with the first segment.

When the second strand of the reagent does not contain the fourth segment, the reagent may be used in particular to transcribe an RNA whose 3' end region, or a region close to the 3' end, has a known sequence, and in this case the second nucleotide segment of the first strand is constructed so that said RNA, in the vicinity of its 3' end, is capable of hybridization with at least part of the sequence of said second nucleotide segment. The 3' end of the part of the RNA to be transcribed which is hybridized to the second segment may be contiguous to the 5' end of the third segment, or it may be distant therefrom by a number x of nucleotides (counted on the second segment), x representing zero or an integer from 1 to 24. Of course, the length of the second segment (in number of nucleotides) is greater than x, in order to be able to ensure the binding of the RNA template to be transcribed, by hybridization with a downstream region of the second segment.

The fourth segment, containing for example from 1 to 18 nucleotides, and in particular from 1 to 12 nucleotides, preferably has a sequence chosen so as to favor the initiation of transcription for a given RNA polymerase (see in particular the experimental section below). The fourth segment may be produced in particular in DNA. Its sequence may be complementary to the upstream region of the second segment facing it and to which it is then hybridized. In this case, the choice of the sequence of the 5' region of the second segment is dictated by the choice of the sequence of the fourth segment. It is not necessary for the fourth segment to be linked to the third segment since in any case its correct positioning in order to favor the initiation of transcription may be ensured by its hybridization to the second segment. However, in a specific embodiment, the fourth segment is linked to the third segment.

As above, the 3' end of the target RNA part which is hybridized with the second segment may be distant from the 5' end of the fourth segment by a number of nucleotides equal to x, as defined above.

For obvious reasons, the second segment contains a number of nucleotides at least equal to the sum of the number of nucleotides of the fourth segment, if it is present, and of the number of nucleotides of said sequence of the second segment which is capable of hybridizing with said region of the RNA to be transcribed.

The method of transcription of the invention may be carried out with a virus or phage wild-type RNA polymerase, and in particular with an RNA polymerase chosen from the family of RNA polymerases, mentioned above, which includes the T7 RNA polymerase, T3 RNA polymerase and SP6 RNA polymerase.

It has indeed been discovered that these RNA polymerases, known to be DNA-dependent, were also capable of transcribing an RNA template, optionally choosing (for example by virtue of the fourth segment described above) a sequence favoring the initiation of transcription.

The discovery of this RNA-dependent RNA polymerase activity makes it possible to have for the first time RNA polymerases capable of transcribing RNA under the control of a promoter, starting from position +1, and in the absence of associated protein factor.

It is also possible to carry out the method of the invention with mutated RNA polymerases which will be described in greater detail below. The importance of these mutated RNA polymerases is that some of them are capable of carrying out the transcription with a better yield when the template consists of RNA than when the template consists of a comparable DNA (that is to say containing deoxyribonucleotides A, C, G in place of the ribonucleotides A, C, G, respectively, and containing the deoxyribonucleotide T in place of the ribonucleotide U).

The invention also relates to the use of an RNA polymerase capable of transcribing an RNA template, under the control of a promoter, in the absence of, auxiliary protein factor, in a method of transcription of a template strand comprising an RNA target sequence in which said RNA polymerase is chosen from the T7 RNA, the SP6 RNA polymerase and the mutated RNA polymerases as defined above. The template strand may consist of RNA, or may consist of DNA in the region for initiation of transcription, and then of RNA next.

The invention also relates to the use of an RNA polymerase capable of transcribing an RNA template, under the control of a promoter, in the absence of auxiliary protein factor, in a method of transcription of a template strand comprising an RNA target sequence, in which said template strand consists of RNA at least between position +5 and the 5' end of the target. The template strand therefore consists of RNA starting from one of the positions +1 to +5, and may therefore consist of DNA from position +1 to position +2, +3 or +4. The article by S. Leary et al. mentioned below describes the transcription of a template consisting of DNA for positions +1 to +6 and then of RNA for positions 7 and the next ones, with T3 RNA polymerase.

The invention also relates to the RNA-dependent RNA polymerases (RNAdRNAp) obtained by modification of DNA-dependent RNA polymerases and which are capable of synthesizing RNA strands complementary to an RNA template. They may be used, for example, in the sequencing of RNA, the synthesis of RNA probes, and amplification techniques allowing in particular the detection and quantification of RNA.

The known natural RNAdRNAp are not suitable for use as polymerases in several applications because they have acquired a strong discriminatory capacity with respect to their specific RNA template. Furthermore, these enzymes have not been well characterized. For the majority, they form supramolecular complexes composed of both viral and cellular factors; these complexes, which are generally associated with the membranes, are difficult to purify and are unstable during isolation (B. N. Fields, D. M. Knipe, *Virology, Vols* 1 and 2, Raven Press, New York, (1990); G. P. Pfeifer, R. Drouin, G. P. Holmquist, *Mutat. Res. Fundam. Mol. Mech. Mutagen.* 288, 39 (1993)).

Few RNAdRNAp have been cloned, sequenced and expressed. The enzyme Qβ replicase is the best characterized. This enzyme is composed of 4 subunits, of which 3 are host factors (M. Kajitarii, A. Ishihama, *Nucleic Acids Res.* 19, 1063 (1991)). The Qβ enzyme has been isolated; it shows good processability and is capable of carrying out cyclic reactions (P. M. Lizardi, C. E. Guerra, H. Lomeli, I. Tussie-Luna, F. R. Kramer, *Bio/Technology* 6, 1197 (1988)). However, this enzyme remains very limited in its applications because it recognizes as template only a restricted class of highly structured RNA molecules (V. D. Axelrod, E. Brown, C. Priano, D. R. Mills, *Virology* 184, 595 (1991)).

Another RNAdRNAp has been partially characterized. It is an enzyme from the *Saccharomyces cerevisiae* L-A virus. This polymerase, which has been cloned, requires assembling of the viral particle; it binds first of all to the plus RNA strand, and then induces the assembly of the proteins of the particle (T. Fujimura, R. Esteban, L. M. Esteban, R. B. Wickner, *Cell* 62, 819 (1990)). At least three factors are known to combine with the viral particles. These factors are necessary for the replication of RNA, for transcription and for the coherent maintenance of the particle (T. Fujimura, R. B. Wickner, *Molec. Cell. Biol.* 7, 420, (1987)). Studies in vitro have shown that an intact viral particle is necessary for the synthesis of the minus strand (replication) (T. Fujimura, R. B. Wickner, *Cell* 55, 663 (1988)) and for the synthesis of the plus strand (transcription) (T. Fujimura, R. B. Wickner, *J. Biol. Chem.* 264, 10872 (1989)). Thus, the complexity of this system does not make it easily adaptable to an in vitro transcription system. Furthermore, just like the Qβ system, this system is very discriminatory, accepting only M and L-A viral RNAs as template (T. Fujimura, R. B. Wickner, *Cell* 55, 663 (1988)).

An RNAdRNAp for which a broad template accepting capacity has been shown is the enzyme of the poliomyelitis virus (J. Plotch, O. Palant, Y. Gluzman, *J. Virol.* 63, 216 (1989)). However, several problems exist with this enzymatic system: the priming is dependent either on an unidentified host factor or on the addition of a poly(U) oligonucleotide. However, given that priming with a poly(U) oligonucleotide is not selective with respect to the template, many products of different sizes are synthesized, in particular products having twice the length of the template. Furthermore, the sequential synthesis of the plus and minus strands has not been demonstrated (S. J. Plotch, O. Palant, Y. Gluzman, *J. Virol.* 63, 216 (1989), T. D. Hey, O. C. Richards, E. Ehrenfeld, *J. Virol.* 61, 802 (1987), J. M. Lubinski, L. J. Ransone, A. Dasgupta, *J. Virol* 61, 2997 (1987)).

Among the DNAdRNAp polymerases, the enzymes of the T3 and T7 bacteriophages are capable of using RNA as template under particular conditions. For example, the T3 DNAdRNAp may transcribe a single-stranded RNA template (i.e. the messenger RNA for the gene for resistance to neomycin) if it is ligated to the antisense strand of the T3 promoter including the sequence for initiation from +1 to +6 (S. Leary, H. J. Baum, Z. G. Loewy, Gene 106, 93 (1991)). It is also known that the T7 RNA polymerase can transcribe, from one end to the other, an RNA template in the absence of the promoter sequence (M. Chamberlin, J. Ring, J. Biol. Chem. 248, 2235 (1973)). Furthermore, it has been shown that the T7 RNA polymerase can efficiently transcribe two small specific RNA templates, the "X" and "Y" RNAs, producing both plus and minus RNA copies. This replication, which is obtained in the absence of a consensus promoter sequence, appears to be dependent on the presence of a specific secondary structure (M. M. Konarska, P. A. Sharp, Cell 57, 423 (1989), M. M. Konarska, P. A. Sharp, Cell 63, 609 (1990)). On the other hand, the "X" and "Y" RNAs are not replicated by the T3 RNA polymerase, and it is not known if this enzyme is not capable of replicating highly structured RNAs, or if the sequence specificity of this enzyme prevents its recognition of the "X" and "Y" RNAs. In the absence of a promoter, it has also been shown that the T7 DNAdRNAp was capable of carrying out the extension of two overlapping RNA strands in antisense (C. Cazenave and O. C. Ulhlenbeck, Proc. Natl. Acad. Sci. USA 91, 6972 (1994)). Likewise, it has been shown that the wild-type T7 DNAdRNAp is capable of carrying out the extension of an RNA primer on a single-stranded DNA template, in the absence of a promoter (S. S. Daube and P. H. von Hippel, Biochemistry 33, 340 (1994)).

The best characterized bacteriophage enzyme is the T7 RNA polymerase, a monomeric enzyme of 98 kDa (B. A. Moffatt, J. J. Dunn, F. W. Studier, J. Mol. Biol. 173, 265 (1984)). This monomeric polymerase has all the essential properties of an RNA polymerase, that is to say recognition of a promoter, initiation of transcription, extension and termination (M. Chamberlin, T. Ryan, The Enzymes XV, 87 (1982)). Furthermore, the catalytic activity requires few elements, namely a template, ribonucleoside triphosphates and the divalent $Mg^{2+}$ ion, and it does not require any auxiliary protein factor for the initiation or termination of transcription, unlike the other RNA polymerases (M. Chamberlin, T. Ryan, The Enzymes XV, 87 (1982)).

Mutagenesis of the T7 RNA polymerase gene has made it possible to identify and to define regions or residues involved in the polymerase function. A mutagenesis strategy has consisted in exchanging elements between the T7 RNA polymerase and its close relative the T3 RNA polymerase whose amino acid sequence is 82% identical (K. E. Joho, L. B. Gross, N. J. McGraw, C. Raskin, W. T. McAllister, J. Mol. Biol. 215, 31 (1990)). This strategy has led to the identification of polymerase elements involved in the recognition of the promoter. It has been shown, for example, that the substitution of a single amino acid in the T3 (or T7) enzyme allows the mutated enzyme to specifically recognize the heterologous T7 (or T3) promoter (C. A. Raskin, G. Diaz, K. Joho, W. T. McAllister, J. Mol. Biol. 228, 506 (1992)). In the same manner, reciprocal substitutions in the respective promoter sequences confer on the mutated promoter the capacity to be recognized by the heterologous enzyme (C. A. Raskin, G. Diaz, K. Joho, W. T. McAllister, J. Mol. Biol. 228, 506, (1992)).

T7 RNA polymerase has been crystallized and its structure determined at a resolution of 3.3 Å (R. Sousa, Y. J. Chung, J. P. Rose, B.-C. Wang, Nature 364, 593 (1993)). From this structural study, sequence alignments (K. E. Joho, L. B. Gross, N. J. McGraw, C. Raskin, W. T. McAllister, J. Mol. Biol. 215, 31 (1990); S. Mungal, B. M. Steinberg, L. B. Taichman, J. Virol. 66, 3220 (1992), W. T. McAllister, C. A. Raskin, Molec. Microbiol. 10, 1 (1993)) and mutagenic studies (D. Patra, E. M. Lafer, R. Sousa, J. Mol. Biol. 224, 307 (1992); L. Gross, W-J. Chen, W. T. McAllister, J. Mol. Biol. 228, 1 (1992)), it has been possible to correlate the functional elements of the T7 enzyme with the structural element. T7 RNA polymerase may be divided into two functional domains: a promoter recognition domain and a catalytic domain (R. Sousa, Y. J. Chung, J. P. Rose, B. -C. Wang, Nature 364, 593 (1993), W. T. McAllister, Cell. Molec. Biol. 39, 385 (1993)).

The T7 RNA polymerase asparagine 748 has been shown to interact with nucleotides −10 and −11 in the promoter sequence, an interaction shown to be responsible for the promoter specificity (C. A. Raskin, G. Diaz, K. Joho, W. T. McAllister, J. Mol. Biol. 228, 506 (1992). The possibility that a sigma-type interaction between the T7 polymerase and its promoter can exist in the bacteriophage system has been mentioned. Indeed, a sigma-type sequence, corresponding to the 2.4 region of sigma, i.e. the region of sigma interacting with the "Pribnow box" (TATAATG sequence recognized by the E.coli sigma 70 transcription factor) (C. Waldburger, T. Gardella, R. Wong, M. M. Susskind, J. Mol. Biol. 215, 267 (1990); D. A. Siegele, J. C. Hu, W. A. Walter, C. A. Gross, J. Mol. Biol. 206, 591 (1989)), exists in the N-terminal region of the T7 RNA polymerase between amino acids 137 and 157 (L. Gross, W -J. Chen, W. T. McAllister, J. Mol. Biol. 228, 1 (1992)). Moreover, although it has not been possible to attribute any function to it, the 230 to 250 region exhibits sequence homologies with the E.coli λ repressor (McGraw, N. J., Bailey, J. N., Cleaves, G. R., Dembinski, D. R., Gocke, C. R., Joliffe, L. K., MacWright, R. S. and McAllister, W. T. Nucleic Acids Res. 13, 6753 (1985)).

The catalytic domain consists of a pocket resulting from the bringing into close proximity of several regions dispersed over the primary structure (R. Sousa, Y. J. Chung, J. P. Rose, B.-C. Wang, Nature 364, 593 (1993), W. T. McAllister, C. A. Raskin, Molec. Microbiol. 10, 1 (1993); D. Moras, Nature 364, 572 (1993)). This pocket contains in particular several conserved motifs among which the A and C motifs are the best conserved in the polymerases (Poch, O., Sauvaget, I., Delarue, M. and Tordo, N. EMBO J. 8, 3867 (1989); Delarue, M., Poch, O., Tordo, N. and Moras, D. Protein Engineering 3, 461 (1990); W. T. McAllister, C. A. Raskin, Molec. Microbiol. 10, 1 (1993)). A third motif, the B motif, is conserved in DNA-dependent RNA and DNA polymerases whereas a B' motif which is different (both for the sequence and for the apparent structure) exists in the RNA-dependent RNA and DNA polymerases (Poch, O., Sauvaget, I., Delarue, M. and Tordo, N. EMBO J. 8, 3867 (1989); Delarue, M., Poch, O., Tordo, N. and Moras, D. Protein Engineering, 3, 461 (1990); L. A. Kohlstaedt, J. Wang, J. M. Friedman, P. A. Rice, T. A. Steitz, Science 256, 1783 (1992); W. T. McAllister, C. A. Raskin, Molec. Microbiol. 10, 1 (1993)).

One of the aspects of the present invention is based on the discovery that certain mutated DNA-dependent RNA polymerases are capable of transcribing a single-stranded or double-stranded RNA in the presence of a double-stranded DNA promoter. Furthermore, these mutant enzymes are not very capable or are incapable of transcribing single-stranded or double-stranded DNA in the presence of a double-stranded DNA promoter. They are therefore preferably or strictly RNA-dependent. Their use is particularly advantageous in cases where it is desired to selectively transcribe the RNA, in particular when the starting biological sample contains or risks containing DNA having a sequence identical or similar to that of the RNA to be amplified.

The subject of the invention is therefore an RNA polymerase capable of transcribing a polynucleotide segment of interest of any sequence contained in a polynucleotide template, by synthesizing, in the presence of said template, and under the control of a promoter, a product of transcription containing an RNA sequence complementary to the sequence of said polynucleotide segment of interest, characterized in that it is capable of synthesizing said product of transcription with a better yield when said sequence of interest contained in the template consists of RNA than when said sequence of interest contained in the template consists of DNA.

The invention relates in particular to an RNA polymerase defined as above such that the ratio of the yield of product of transcription of a DNA template to the yield of product of transcription of an RNA template, expressed in %, is less than 95%, especially less than 85% and in particular less than 70%.

The subject of the invention is in particular an RNA polymerase as defined above, characterized in that the ratio of the yield of product of transcription of the RNA template to the yield of product of transcription of the DNA template is at least equal to 2 and in particular at least equal to 10.

The "yield" of transcription is the molar ratio of the quantity of product of transcription to the quantity of polynucleotide template present at the origin. This yield may be easily determined experimentally, by introducing into the reaction medium a determined quantity of the polynucleotide template. For comparison of the yields obtained with a DNA template and an RNA template, conditions other than those of the nature of the template must obviously be comparable.

The RNA polymerase of the invention is capable of transcribing a polyribonucleotide template of any sequence, and it differs from Qβ-replicase in this respect. It preferentially or exclusively transcribes an RNA template, and it differs from known phage DNA-dependent RNA polymerases in this respect.

The RNA polymerases of the invention, unlike the known natural RNAdRNAP polymerases, are in particular RNA polymerases capable of functioning without associated protein cofactor(s). They may however be provided in the form of multimers, and in particular of dimers.

The mutated RNA polymerases of the invention are therefore generally obtained from RNA polymerases which are themselves capable of functioning without protein cofactors.

The RNA polymerases of the invention may be in particular RNA polymerases which are derived by mutation from a virus or phage DNA-dependent RNA polymerase, and in particular from a DNA polymerase of an *E. coli* phage. Among the *E. coli* phages, there may be mentioned in particular T3, T7 and SP6.

An RNA polymerase according to the invention may possess a protein sequence homology greater than 50%, and in particular greater than 80% with a wild-type RNA polymerase of the family of DNA-dependent RNA polymerases including the T7 RNA polymerase, T3 RNA polymerase and SP6 RNA polymerase.

The abovementioned family of DNA-dependent RNA polymerases is known; see for example the article by R. Sousa, TIBS 21, 186–190 (1996), and the references cited in that article.

Among the polymerases of the invention, there may be mentioned in particular those which contain at least one mutation in a region corresponding to the T7 RNA polymerase sequence containing amino acids 625–652, and in particular those which have the composition of a wild-type DNA-dependent RNA polymerase, with the exception of the fact that they contain at least one mutation in said region. "Mutation" is understood here to mean the replacement, deletion or insertion of an amino acid.

There may be mentioned for example the RNA polymerases containing at least one mutation at a position corresponding to one of positions 627, 628, 631, 632 and 639 of the T7 RNA polymerase amino acid sequence; in particular said mutation may comprise the replacement of an amino acid residue, chosen from arginine, lysine, serine and tyrosine, of the wild-type RNA polymerase with another amino acid residue. The amino acid replaced is for example an arginine or a lysine. The replacement amino acid may be chosen in particular from alanine, valine, leucine, isoleucine, glycine, threonine or serine. It is understood that the expression "amino acid" designates here, by a misuse of language, an amino acid residue engaged in a peptide bond.

Reference was made above to the peptide sequence of the T7 RNA polymerase. The numbering of the amino acid residues adopted here is that described by Dunn, J. J. and Studier, F. W. J. Mol. Biol. 148(4), 303–330 (1981), and by Stahl, S. J. and Zinn, K., J. Mol. Biol. 148(4), 481–485 (1981).

The invention also relates to:

a gene encoding an RNA polymerase as defined above; such a gene may be obtained for example according to a method similar to that described below in the experimental part;

an expression vector into which such a gene is inserted, said vector being capable of expressing said RNA polymerase in a host cell; this vector may be obtained in a manner known per se;

a host cell containing such a vector.

The invention also relates to a method of producing an RNA polymerase as defined above, characterized in that: a) a gene encoding a wild-type RNA polymerase is obtained in a known manner, b) at least one mutation is performed on said gene, c) the mutated gene obtained is inserted into an expression vector, d) said vector is expressed in a host cell in order to obtain a mutated RNA polymerase and e) among the mutated RNA polymerases obtained, those which exhibit at least one of the properties of an RNA polymerase as defined above are selected.

A more detailed description of a particular embodiment of the method of the invention will be given below in the case of the use of the T7 RNA polymerase as starting material.

Figure 1B:
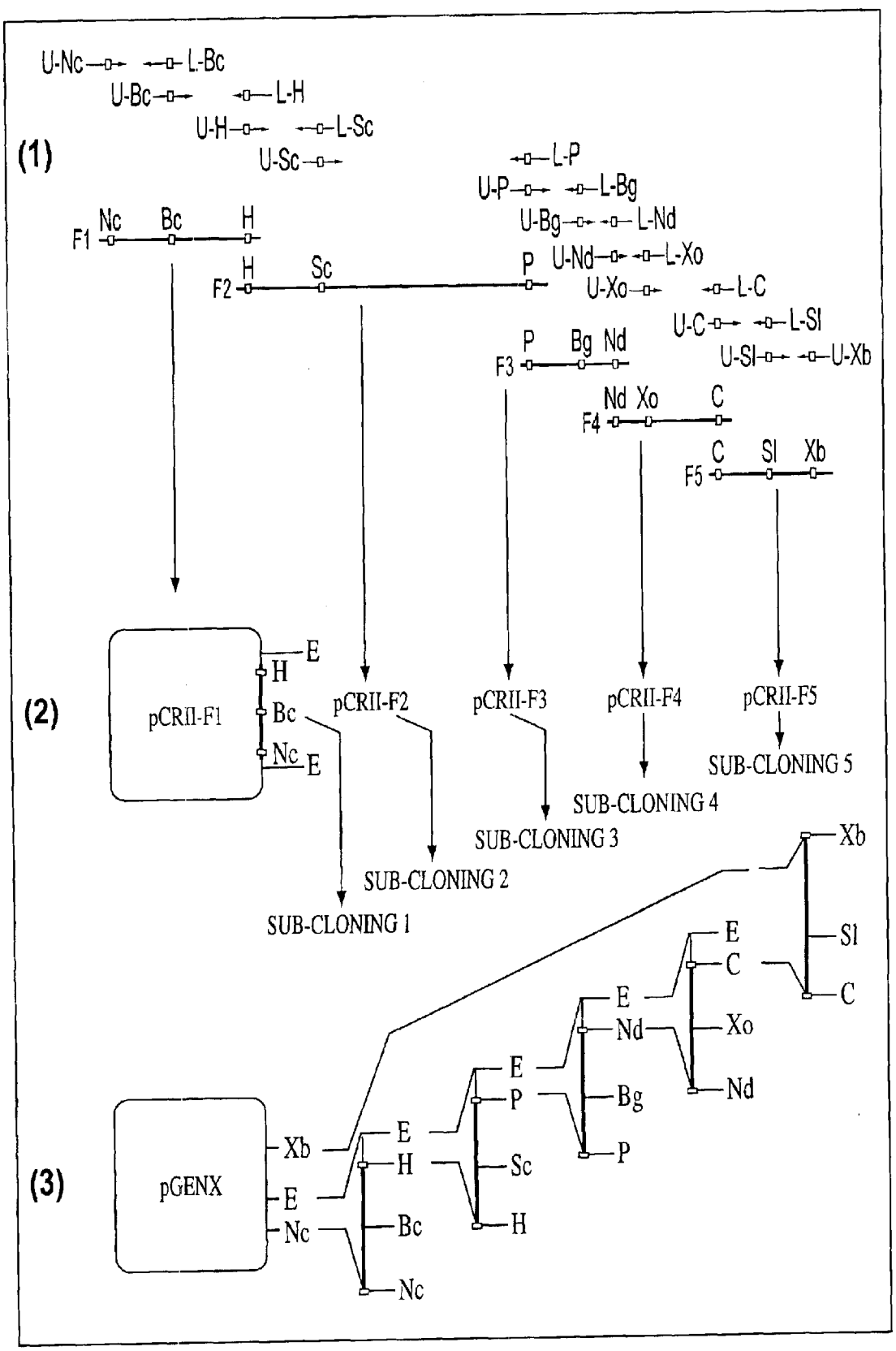
Figure 1C:
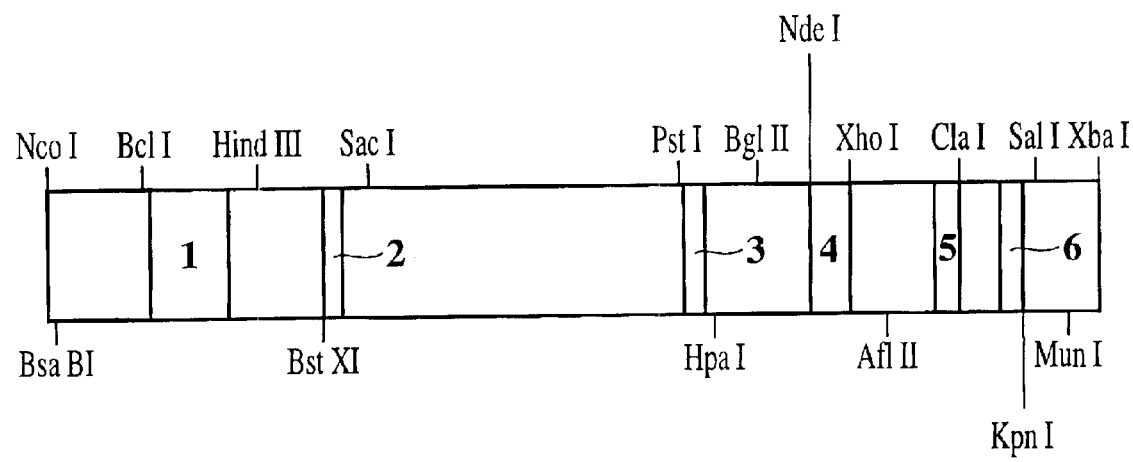

A modular gene for T7 DNAdRNAp was prepared, this gene resulting from the assembly of different cassettes (see Example 1 and FIG. 1).

The modular gene thus defined is characterized in that it contains 10 cassettes bordered by unique restriction sites in the cloning vector.

In particular, these cassettes, bordered by unique restriction sites, are characterized in that each cassette comprises a region of interest, in particular those involved in promoter recognition (region exhibiting homology with the *E. coli* α factor; region exhibiting homology with the *E. coli* σ repressor; region conferring promoter specificity) and those involved in the catalytic site (motif A; motif B; motif C).

For the definition of motifs A, B and C. see for example R. Sousa, TIBS 21, 186–190 (1996).

These cassettes, derived from The T7 DNAdRNAp gene 1, were obtained with the aid of conventional molecular biology techniques (F. M. Ausubel, R. Brent, R. E. Kingston, D. D. Moore, J. G. Seidman, et al. *Current Protocols in Molecular Biology* (Current Protocols, 1993)), in particular PCR, which made it possible to introduce restriction sites by silent site-directed mutagenesis, and subcloning into a cloning vector.

The modular gene thus obtained is characterized by the presence of restriction sites bordering the cassettes, these restriction sites being the Nco I (−2, +4), Bcl I (218, 223), Hind III (539, 544), SacI (776, 781), PstI (1587, 1592), BglII (1811, 1816), NdeI (1865, 1870), XhoI (1951, 1956), ClaI (2305, 2310), SalI (2497, 2502), XbaI (2660, 2665) site; position 1, in nucleic acids, corresponds to the adenine of the initiator ATG codon and position 2652 to the third base of the TAA terminator codon. The NdeI site (2504, 2509) as destroyed. All the mutations inducing these restriction sites are silent, except the mutation generating the NcoI site which induces the replacement of asparagine at position +2 with a glycine. Position 1, in amino acids, corresponds to the first methionine, position 883 corresponds to the carboxy-terminal alanine.

The modular gene, cloned into a cloning vector pGNEX derived from pGEM-1 in which the polylinker has been replaced by an adaptor containing the Nco I, EcoRI, XbaI restriction sites constitutes the basic support for subsequent mutageneses. This is made possible by the fact that each cassette containing a region of interest is bordered by unique restriction sites in the cloning vector.

The introduction of nonsilent mutations, with the aid of PCR techniques, into one or more cassettes of the modular gene previously defined, led to genes encoding polymerases exhibiting an amino acid sequence differing by at least one amino acid with respect to the T7 expressed from the modular gene. Mutant genes were in particular prepared which encode at least one modified amino acid in the B motif of the wild-type enzyme, for example with an alanine (A) in place of an arginine (R) at position 627 and/or an alanine (A) in place of a serine (S) at position 628 and/or an alanine (A) in place of a lysine (K) at position 631 and/or an alanine (A) in place of an arginine (R) at position 632 and/or an alanine (A) in place of a tyrosine (Y) at position 639.

Mutant genes were also obtained which encode a polymerase whose 625VTRSVTKRSVMTLAYGSKEFG-FRQQVLD652 (SEQ ID NO: 6) region comprising the B motif has been replaced as a whole or in part by the homologous region B' present in some RNA-dependent polymerases, in particular those of the polymerases of the hepatitis C virus (NCGYRRCRASGVLTTSCGNTLTCYI) (SEQ ID NO:7), and of the yeast integrase 32 (HNTTLGIPQGSWVSPILCNIFLDKL) (SEQ ID NO:8).

The genes described above have been cloned into a vector pMR resulting from the ligation of the SspI fragment of pMal-c (Biolabs) containing in particular the lacI$^q$ repressor, and of the SspI fragment of pMH (V. Cheynet, B. Verrier, F. Mallet, *Protein expression and purification* 4, 367 (1993)) containing a minicistron making it possible to achieve a high level of expression, as well as a sequence encoding a poly-histidine tail fused with the terminal end of the cloned gene (Example 1, FIG. 2). The expression of the recombinant proteins T7 RNAp into the bacterial strain BL21 represents up to 30% of the total proteins of the bacterium. The proteins solubilized in a deoxycholate buffer containing a high salt concentration are deposited on a TALON column (Clontech) allowing specific purification by chelation with the ion of proteins having a poly-histidine tail. 130 to 2200 µg of polymerases are thus obtained for 20 ml of culture, with a purity greater than 95% as indicated (i) by a Coomassie blue staining (Example 1, FIG. 3), (ii) by a Western-blot analysis with a guinea-pig polyclonal antibody anti-T7 RNAP (bioMérieux) and a mouse monoclonal antibody (Quiagen) anti-MRGSHHHHHH (SEQ ID NO: 9), (iii) by the absence of endonuclease, single-stranded and double-stranded exonuclease or ribonuclease activity, as determined essentially according to the method of He et al (B. A. He, M. Rong, D. L. Lyakhov, H. Gartenstein, G. Diaz, et al, *Protein Expr Purif* 9, 142 (1997)). This result reflects the performances of the host-pMR-BL21 vector pair and of the method of purification with respect to the MRGSHHHHHS-VLE (SEQ ID NO: 10) tail.

The subject of the invention is also the use of an RNA polymerase as defined above, in a method of transcription of a polynucleotide segment of interest having any sequence, said segment, of the RNA type, being contained in a polynucleotide template, so as to synthesize, in the presence of said template, a product of transcription containing an RNA sequence complementary to the sequence of said polynucleotide segment of interest.

According to a particular embodiment, said use is characterized in that said polynucleotide template comprises, upstream of said polynucleotide segment of interest, a promoter recognized by said RNA polymerase, and in that said product of transcription is an RNA complementary to a sequence of the template starting at a site of initiation of transcription for said promoter.

The RNA polymerases of the invention may be used in particular to carry out (i) an amplification of an RNA target isothermally, (ii) a direct sequencing of, RNA and (iii) the synthesis of RNA of special interest (for example probes, ribozymes and the like). In addition, RNA polymerases of the invention are capable of incorporating modified bases into the newly-synthesized strand, which facilitates in particular the quantification or the use of said strand.

The invention relates in particular to the use of these recombinant enzymes thus expressed and purified in a method of synthesizing RNA from an RNA template, under the control of a promoter.

The enzymes thus purified were evaluated, in a promoter-dependent context, on different templates (Example 2, FIG. 4 on the one hand, and Example 3, FIG. 6, on the other hand) in particular a template containing a single-stranded RNA. It has been shown that a mutated polymerase obtained according to the invention was capable of generating a specific transcript of the correct size in particular on a single-stranded RNA template. In Example 2, it is indicated that the wild-type enzyme identically produced does not appear to be able to carry out this phenomenon. However, Example 3 shows that the wild-type enzyme in fact possesses the property of transcribing an RNA template. These apparently divergent results are explained by the fact that the experimental conditions in these two examples are different. Indeed, in Example 2, the presence of the transcript is identified by the technique of incorporating a UTP, labeled with radioactive phosphorus, whereas in Example 3 the technique used is Northern blotting for the group 2 templates, and in the latter case, the detection of the transcript by the Northern blotting technique is 40 times more sensitive than the detection by incorporation of radioactive phosphorus. Example 2 below therefore shows that a mutated polymerase obtained according to the invention is capable of generating a specific transcript of the correct size on a single-stranded RNA template, and Example 3 shows that in fact the corresponding wild-type polymerase is capable of generating a specific transcript of the correct size on RNA templates independently of their sequence.

Furthermore, such a mutated polymerase is incapable, unlike the wild-type polymerase, of generating a transcript of the correct size on a single-stranded or double-stranded DNA template. If the $Mg^{2+}$ ion present in the reaction medium is replaced by the $Mn^{2+}$ ion, the mutated enzyme, on a single-stranded RNA template, does not generate under these conditions a specific transcript of the correct size, but is nevertheless capable of generating large quantities of abortive products. Such a mutated polymerase is in addition capable of displacing an RNA/RNA hybrid.

Figure 2:
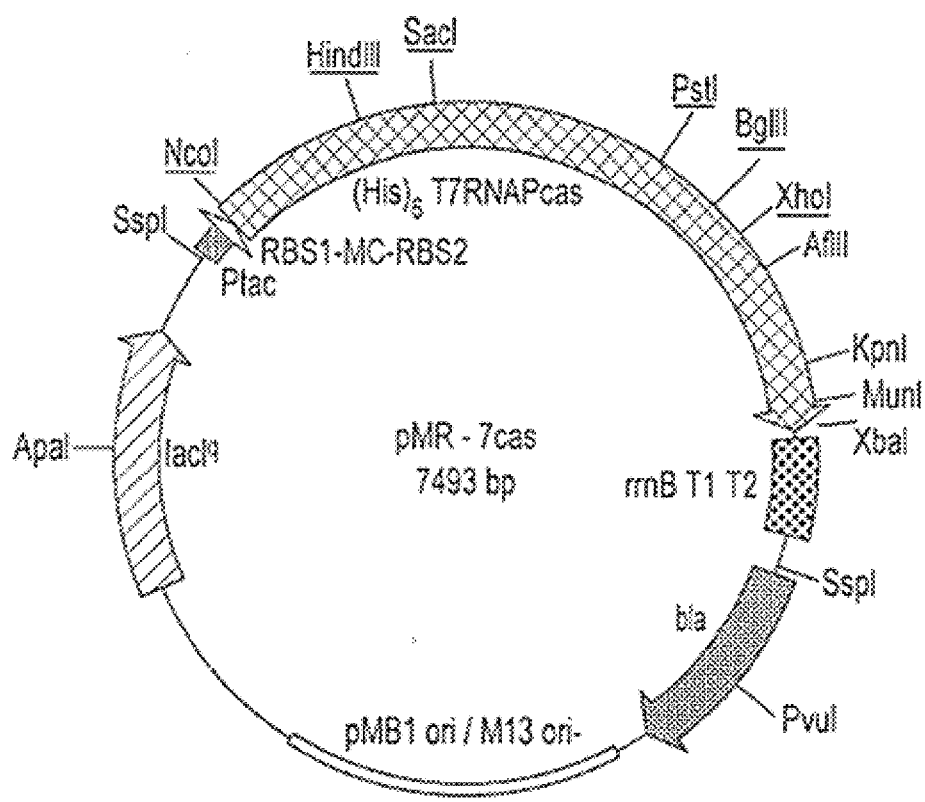
Figure 3:
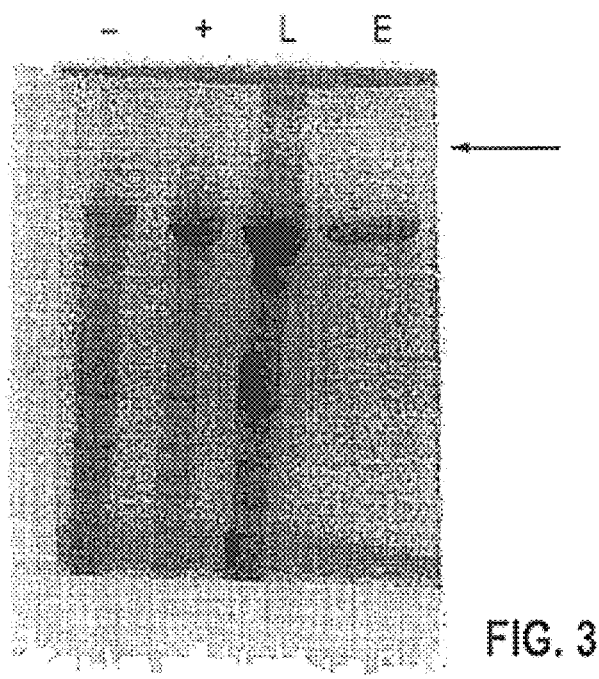
Figure 4:
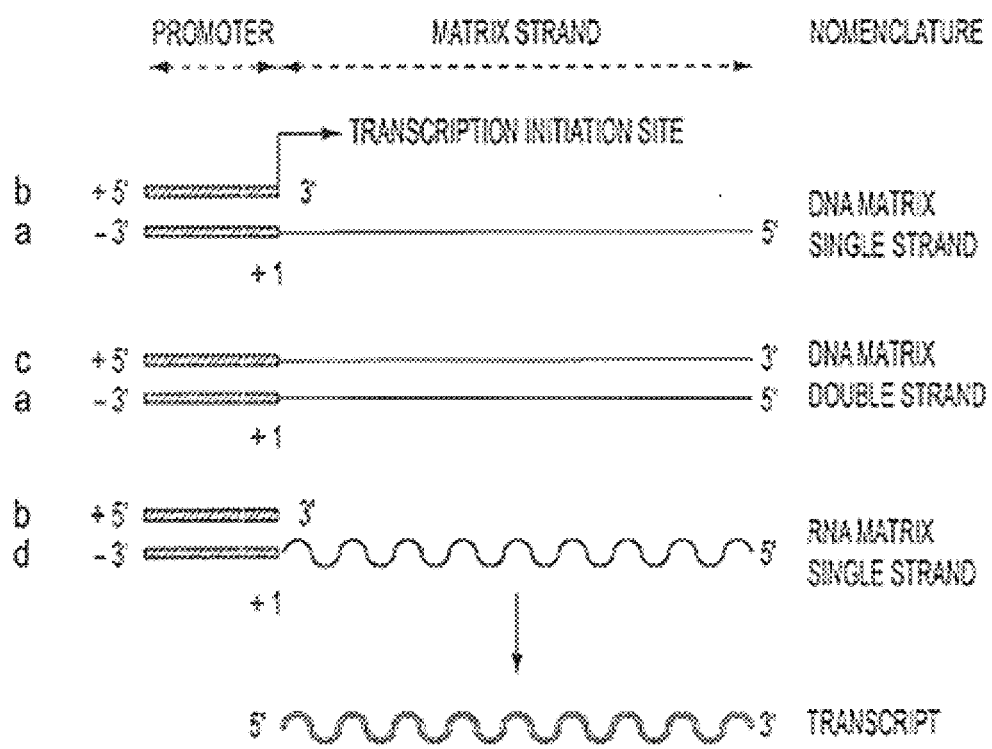
Figure 5:
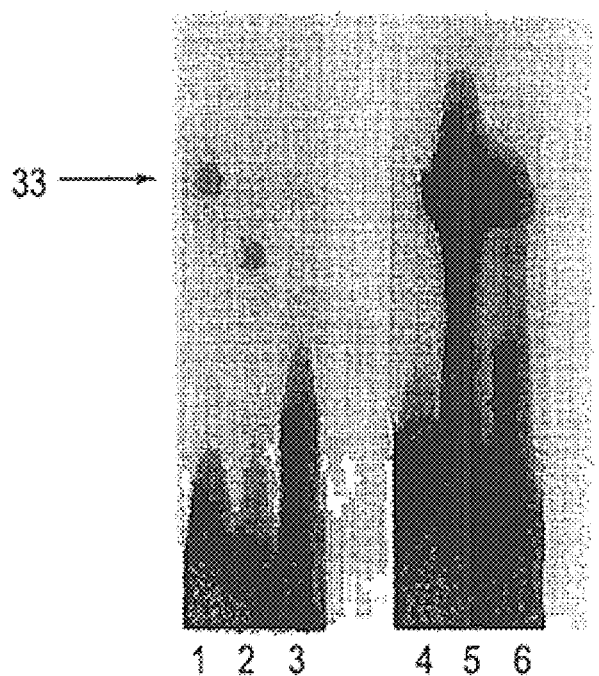
Figure 6:
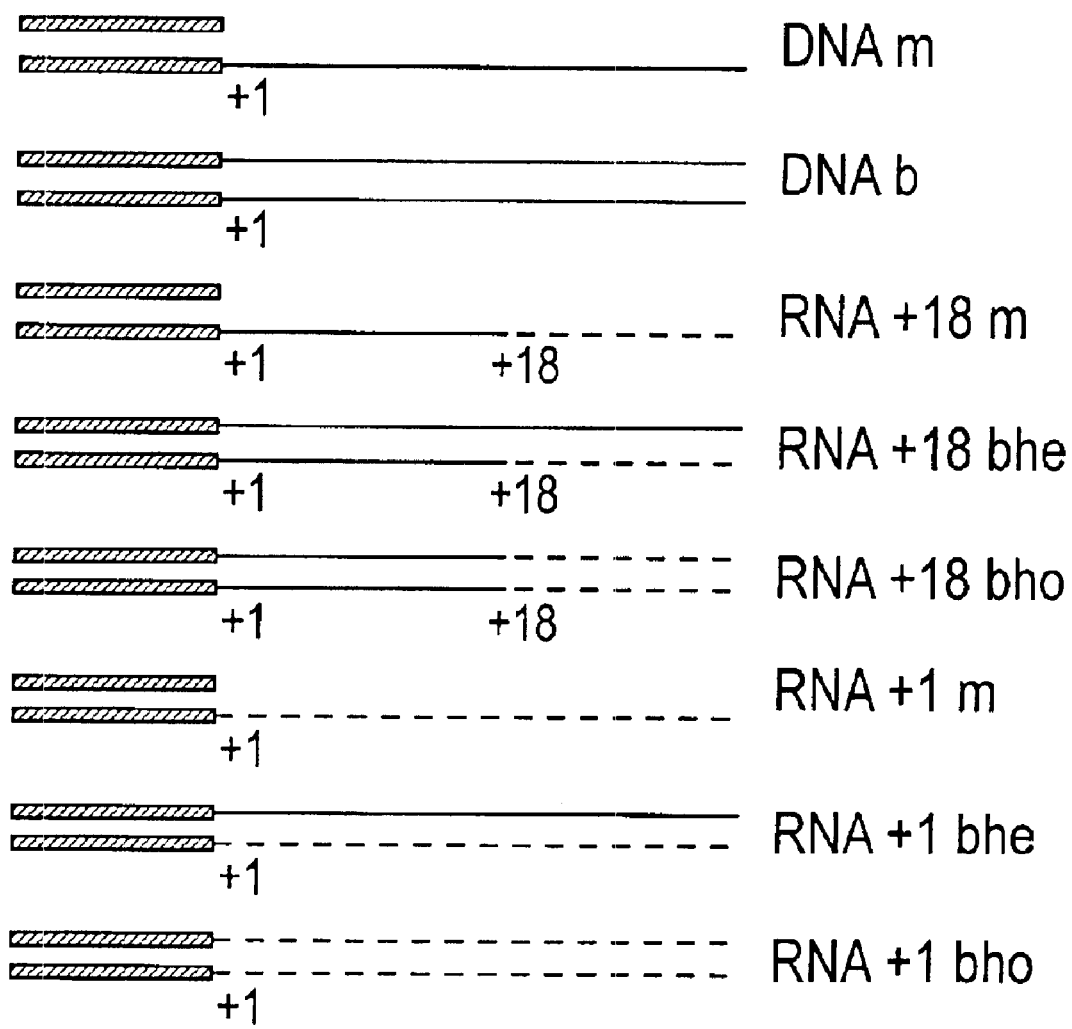

In the appended drawings:

FIG. 1 illustrates the amplification strategy, described in detail in Example 1 below, for the construction of a modular gene for the T7 RNA polymerase, FIG. 2 illustrates the structure of the expression vector pMR containing this modular gene, FIG. 3 represents electrophoretic profiles of the proteins expressed with the aid of this vector, as described in detail in Example 1 below, FIG. 4 schematically represents the template systems used in the transcription trials of Example 2 below, FIG. 5 represents the electrophoretic profiles of the products of transcription obtained in Example 2 below, and FIG. 6 schematically represents the template systems used in the transcription trials of Example 3 below.

The following examples illustrate the invention.

EXAMPLES

Example 1

Construction of the Gene for T7 RNA Polymerase in Modular Form; Expression and Purification of the T7 RNA Polymerase The T7 RNA polymerase gene was constructed in modular form, taking into account the regions of homology with the other polymerases as well as the functions associated with certain domains of T7 RNA polymerase. It was divided into 10 regions or cassettes (FIG. 1-A), each region being delimited by unique restriction sites in the cloning vector. Six cassettes are characteristic in that they contain respectively a domain having similarity with part of the *E. coli* sigma factor, a domain having homology with the *E. coli* lambda repressor, a domain involved in the phage polymerase promoter specificity, the A and C motifs conserved in the template-dependent polymerases and the B motif conserved in the DNA-dependent polymerases. Each region is amplified by PCR (F. M. Ausubel, R. Brent, R. E. Kingston, D. D. Moore, J. G. Seidman, et al, *Current Protocols in Molecular Biology* (Current Protocols, 1993)) (FIG. 1a-B1) from the wild-type gene (gene 1) using primers defined as follows: (i) these primers contain silent mutations allowing the introduction of restriction sites delimiting the cassettes; (ii) the primer situated at position 3' of one region and the primer situated at position 5' of the contiguous region partially overlap. The contiguous amplification products are mixed and reamplified using external primers (FIG. 1a-B1). The 5 fragments generated are cloned into the vector PCRII (Invitrogen) (FIG. 1-B2). From the 5 cloned fragments, the T7 RNA polymerase gene was reconstructed from the 5' end to the 3' end by successive subclonings into the cloning vector PGNEX (FIG. 1-B3). This vector is derived from the plasmid pGEM-1 (Promega) in which the polylinker is replaced by an adaptor containing the NcoI-EcoRI-XbaI restriction sites. The modular gene for T7 RNA polymerase (T7 RNA pol) thus obtained contains 17 unique cloning sites in pGNEX of which 11 newly-introduced sites (FIG, 1-C). This gene was then subcloned into the expression vector pMR (FIG. 2). This vector, derived from the vector pMH (V. Cheynet, B. Verrier, F. Mallet, *Protein expression and purification* 4, 367 (1993)), contains the strong tac promoter regulated by IPTG (isopropyl-beta-D-thiogalactopyranoside), a short minicistron surrounded by two ribosome-binding sites constituting an efficient context for initiation of translation and a polyhistidine tail fused with the N-terminal end of the expressed protein allowing its purification by metal ion-affinity chromatography. The gene encoding the lacI$^q$ repressor allowing a better control of expression is also present in pMR. This expression vector is transformed according to conventional methods (F. M. Ausubel, R. Brent, R. E. Kingston, D. D. Moore, J. G. Seidman, et al, *Current Protocols in Molecular Biology* (Current Protocols, (1993)) in the *E. coli* BL21 bacterial strain. A preculture is used to inoculate 30 ml of culture medium. The expression of the proteins is induced by IPTG for 4 h at 37° C. as soon as the optical density at 600 nm of the culture reaches 0.6. The T7 RNA pol thus expressed represents 30% of the total bacterial proteins (FIG. 3). It is then extracted from the bacteria by lysis (sonication) in the presence of a detergent. From the soluble extracted fraction, the T7 RNA pol is purified by $Co^{2+}$-ion affinity chromatography and eluted with an imidazole gradient. It is analyzed on an SDS-PAGE gel and visualized by Coomassie blue staining (FIG. 3). The absence of degradation products is verified by Western blotting with a polyclonal antibody anti-T7 RNA pol produced in guinea-pigs and a monoclonal antibody anti-MRGSH$_6$ which is commercially available (Quiagen). The absence of spurious endonuclease, exonuclease and RNase activities is verified according to the protocol described by He et al, *Protein Expr Purif* 9, 142 (1997)). From 20 ml of culture 700 to 800 µg of enzymes, having a purity greater than 95%, are obtained in a reproducible manner. The purification yield is 75%.

The point mutations are created by sequential PCR (F. M. Ausubel, R. Brent, R. E. Kingston, D. D. Moore, J. G. Seidman, et al, *Current Protocols in Molecular Biology* (Current Protocols, (1993)) (or double PCR), in the same manner in which the restriction sites were introduced: the internal primers contain the mutation to be introduced; the external primers flank the region to be mutated and contain the restriction sites delimiting this region in the modular gene. This cassette thus mutated is then cloned into the modular gene. Synthetic oligonucleotides may also replace a complete cassette.

Legend to the Figures Mentioned in Example 1

FIG. 1: illustrates the amplification strategy for the construction of the modular gene for the T7 RNA polymerase. (A): Division of the T7 RNA polymerase gene (vertical arrows) with respect to the regions of interest. The regions marked from 1 to 6 are: 1, homology with part of the *E. coli* sigma factor; 2, homology with the *E. coli* lambda repressor; 3, motif A; 4, motif B; 5, phage polymerase promoter specificity; 6, motif C. (B): (1) Position of the primers containing the silent mutations for the creation of the restriction sites (-□-); Nc, NcoI; Bc, BclI; H, HindIII; Sc, SacI; P, PstI; Bg, BglII; Nd, NdeI; Xo, XhoI; C, ClaI; Sl, SalI; Xb, XbaI. Extension by overlapping PCR leads to 5 fragments containing 3 restriction sites (F1 to F5). Subcloning means: subcloning. (2) Each fragment thus generated (F1 to F5) is cloned into the vector PCRII. E, EcoRI. (3) Reconstruction of the modular gene from the 5' end to the 3' end, using at each step the restriction site common to 2 fragments and the EcoRI restriction site of the vector PCRII and of the cloning vector pGNEX; the XbaI restriction site common to the last fragment and to the vector pGNEX is used for the last subcloning. (C) structure of the modular gene for T7 RNA polymerase and position of the unique restriction sites in the vector pGNEX which already exist (at the bottom) and created by mutagenesis (at the top).

FIG. 2: illustrates the structure of the expression vector pMR containing the modular gene for T7 RNA polymerase. Ptac: tac promoter (black box); RBS1-MC-RBS2, minicistron surrounded by 2 ribosome-binding sites (white arrow); (His)6T7RNAPcas, modular gene for T7 RNA polymerase (gray arrow); rrnB T1 T2, strong transcription terminators (box with dotted lines); bla, gene for resistance to ampicillin (black arrow); pMB1 ori/M132 ori-, replication origins (thin white box); lacI$^q$, gene encoding the lacI$^q$ repressor (hatched arrow); some restriction sites are indicated, including the new sites introduced by mutagenesis (underlined).

FIG. 3: shows the electrophoretic profiles obtained allowing analysis of the expression and of the purification of the T7 RNA polymerase. The bacterial lysates are prepared from 1 ml collected from 30 ml of culture in order to verify the expression of T7 RNA polymerase in the presence (+) or absence (−) of IPTG. The T7 RNA polymerase is extracted from 20 ml of the same culture. The soluble fraction is loaded onto the purification column (lane L) and the T7 RNA polymerase is eluted (lane E) with an imidazole gradient. M, molecular weight marker. The proteins are visualized on a 10% SDS-PAGE gel by Coomassie blue staining. The arrow indicates the position of the T7 RNA polymerase.

Example 2

Transcription of RNA and DNA Templates by the Mutated T7 RNA Polymerase R627A Under the Control of a Promoter The template systems used in this example are schematically presented in FIG. 4. The single-stranded DNA transcription system comprises a template strand (a) of 50 bases having the sequence 3'ATTATGCTGAGTGATATC-CCAACCGGCGTCACAAGTGAGTACCAATACCG5' (SEQ ID NO: 2) and hybridized from positions −17 to +1 with the non-template promoter strand (b) having the sequence 5'TAATACGACTCACTAG 3' (SEQ ID NO: 11) (blocked at its 3' end). The double-stranded DNA transcription system comprises the template strand (a) hybridized with the non-template strand (c) having the sequence 5'TAATACGACTCACTATAGGGTTGGCCG-CAGTGTTCACTCATGTTATGGC3' (SEQ ID NO: 12).

The single-stranded RNA transcription system consists of a DNA hybrid strand from positions −17 to −1 and RNA from positions +1 to +33 having the sequence 3'ATTAT-GCTGAGTGATATCCCAACCGGCGUCA-CAAGUGAGUACCAAUACCG5' (SEQ ID NO: 13), hybridized with the non-template promoter strand (b). The expected complete transcripts on the three systems are of 33 bases.

The reactions are performed in 20 µl of a buffer derived from that described by J. F. Milligan, D. R. Groebe, G. W. Witherell, O. C. Uhlenbeck, Nucleic Acids Res. 15, 8783 (1987), namely Tris-HCl 40 mM, pH 8.1, spermidine 1 mM, PEG 8% (g/V), TRITON X-100 (Octoxynol-9) 0.01% (V/V), BSA 5 µg/100 µl, 1 µl (40 u) of porcine RNAguard (Pharmacia Biotech), UTP 12.5 µM, a 32P UTP 0.5 µCi (Amersham, 10 mCi/ml 400 Ci/mmol) 0.4 mM of the three ribonucleoside triphosphates A, G, C, Mg(OAc)$_2$ 6 mM. The template concentration is set at $10^{11}$ copies of each strand in 20 µl of reaction. The wild-type T7 RNA polymerase is used at 0.5 µM (100 ng/20 µl), the mutated T7 RNA polymerase R627A at 3.65 µM (730 ng/20 µl). Before adding the enzymes, the reactions are denatured for 5 minutes at 65° C. in a heating block and then gradually brought to 37° C. The reactions are initiated by the addition of the polymerases, incubated for 1 hour at 37° C. and then stopped by the addition of an equal volume of 2× blue formamide (formamide 90%, EDTA 25 mM, xylene cyanol 0.02%, bromophenol blue 0.02%) and denatured for 5 minutes at 95° C. 20 µl of each reaction are deposited on a denaturing gel (20% acrylamide, urea 7 M, 1×TBE), and then after migration, the gel is autoradiographed at −70° C. on a Biomax MR film (Kodak). The results (electrophoretic profiles) are presented in FIG. 5, and in particular the transcription results obtained with the mutated T7 RNA polymerase R627A (wells 1–3) and the wild-type T7 RNA polymerase (wells 4–6), on the single-stranded RNA templates (wells 1 and 4), double-stranded DNA (wells 2 and 5), and single-stranded DNA (wells 3 and 6). The transcription on single-stranded RNA, detected by detection of a complete transcript of 33 bases, is possible using the mutated T7 RNA polymerase R627A (well 1) and not the wild-type enzyme (well 4) which produces on the other hand many abortive transcripts; see nevertheless the different results obtained in Example 3 below. The mutated T7 RNA polymerase R627A exhibits a residual transcription activity on double-stranded DNA (well 2), characterized by the presence of a predominant transcript which is smaller in size than the expected transcript, and the presence of a small quantity of abortive products. On single-stranded DNA (well 3), this transcript of abnormal size disappears, whereas the quantity of abortive products increases. By contrast, the wild-type enzyme allows the production of specific transcripts in the presence of DNA templates (wells 5 and 6), this enzyme exhibiting, moreover, a better transcription activity on the double-stranded DNA template (well 5) than on the single-stranded DNA template (well 6); for these two templates, the wild-type enzyme induces the synthesis of numerous abortive transcripts. These results show that the replacement of the arginine 627 by an alanine confers on the mutant enzyme the possibility of synthesizing RNA from an RNA template and induces the loss of capacity to synthesize RNA from a DNA template.

Example 3

The T7 RNA polymerase obtained as in Example 1 is purified by affinity chromatography according to the method described by Arnaud N. et al., Gene, 199, 149–156 (1997).

The purified T7 RNA polymerase has a specific activity of about 200 U/µg.

The sequences of the templates used for the transcription are described in Table 1 below.

In the trials described below, the templates of sequence 1, 2 and 3 of Table 1 are called group 1, group 2 and group 3 templates, respectively.

The sequence of the probes used is represented in Table 1 (sequences Nos. 4 and 5).

Sequence No. 4 recognizes the 3' end of the products of transcription obtained with the templates of groups 1 and 3, and sequence No. 5 recognizes the 3' end of the products of transcription of the group 2 template.

The probes are labeled with $\gamma^{32}$P ATP using T4 polynucleotide kinase or with a $\alpha^{32}$P ddATP using a deoxynucleotide terminal transferase.

Transcriptional Trials

The reactions are carried out in a volume of 20 µL containing 40 m/M Tris-HCl, 1 mM spermidine 50 µg/ml of bovine serum albumin, 0.01% (v/v) Triton X100, 80 mg/ml PEG 8000, 1 µl RNAguard (Pharmacia), 6 mM magnesium acetate, $10^{11}$ copies of template and non-template strands, the nucleoside triphosphates necessary for the transcription and the nucleoside triphosphates labeled as indicated. When the labeled nucleoside triphosphate is $\alpha^{32}$P ATP, concentrations of 0.4 mM UTP, CTP and GTP, 12.5 μM ATP and 0.5 μCi α$^{32}$P ATP (New England Nuclear-Dupont, 800 Ci/mmol) are used. When the labeled nucleoside triphosphate is α$^{32}$P UTP, concentrations of 0.4 mM ATP, CTP and GTP, 12.5 μM of ATP and 0.5 μCi α$^{32}$P UTP (Amersham, 400 Ci/mmol) are used. When the labeled nucleoside triphosphate is γ$^{32}$P GTP, concentrations of 0.4 mM ATP, UTP, CTP and GTP, and 20 μCi γ$^{32}$P GTP (Amersham, 5000 Ci/mmol) are used.

The samples are heated for 5 minutes at 70° C. and then slowly cooled to 37° C. in order to allow the hybridization of the template and non-template strands. 260 ng of T7 RNA polymerase are then added and the mixture is incubated for 1 hour at 37° C. The reactions are stopped by adding an equal volume of 2×buffer (90% formamide, 25 mM EDTA, 0.02% xylene cyanol, 0.02% bromophenol blue). The products of transcription are analyzed by electrophoresis, after heating for 5 minutes at 95° C., on a 20% denaturing polyacrylamide gel, and examined by autoradiography.

For the Northern blot analysis, the reactions are carried out under the same conditions, but without the labeled nucleotides. After migration on a 20% denaturing polyacrylamide gel, the samples are transferred onto nylon membrane (Appligene) and the products of transcription are detected by the appropriate labeled probe and are examined by autoradiography.

Definition of Short Synthetic Templates

Three types of short synthetic templates, containing a double-stranded DNA promoter, were defined in order to verify if the T7 RNA polymerase is capable of using an RNA template in a transcription reaction.

The first type of templates (RNA+18) was defined so as to study the capacity of the T7 RNA polymerase to transcribe an RNA template during the so-called processive phase. This first type of template comprises a double-stranded promoter followed downstream by a chimeric DNA-RNA sequence whose transition is situated 18 bases downstream of the site of initiation of transcription.

The second type of templates (RNA+1) was defined so as to study the capacity. of the T7 RNA polymerase to transcribe an RNA template during the start of transcription phase. This second type of templates comprises a double-stranded promoter followed by an RNA sequence.

The third type of templates (DNA), which serves as a comparison, comprises a double-stranded promoter followed downstream by a DNA sequence.

To study the influence of the non-template strand, the DNA, RNA+18 and RNA+1 templates may be either single-stranded (m), or double-stranded heteroduplexes (bhe), or double-stranded homoduplexes (bho). The double-stranded homoduplex template RNA+18 forms an RNA-RNA duplex starting from position +18. Likewise, the double-stranded homoduplex template RNA+1 forms an RNA-RNA duplex starting from the transcriptional start site.

It should be noted that in Table 1, the different nucleotides have been represented with the letters A, T, C, G. When the template, or part of the template, is DNA, these letters represent deoxyribonucleotides. When the template, or part of the template, is in the form of RNA, these letters represent ribonucleotides and it should be understood that the symbol T is then used in place of the symbol U.

The different transcription systems which have just been mentioned are schematically represented in the appended FIG. 6 in which, for each double-stranded system, the top strand is the non-template strand and the bottom strand is the template strand. The DNA double-stranded promoter region is represented by a thick line. The DNA strands are represented by a thin line, the RNA strands are represented by a discontinuous line. The expression +1 corresponds to the transcriptional start site. The expression +18 corresponds to the eighteenth base downstream of the transcriptional start site. In the representation of these various transcription systems, the letter m means single-stranded; the letter b means double-stranded; bhe means double-stranded heteroduplex; and bho means double-stranded homoduplex.

The transcription systems of FIG. 6 were used with each of the templates, or, depending on the cases, with some of the templates of Table 1. The group 1 templates, using sequence No. 1, correspond to a double-stranded DNA promoter sequence followed by a consensus region of initiation +1 to +6 (Dunn and Studier, J. Mol. Biol., 166, 477–535, 1983), itself followed by a sequence of twenty-six bases downstream.

The group 2 templates correspond to a double-stranded DNA promoter sequence followed by a nonfavorable sequence, since it can allow the early termination of transcription (Martin et al., *Biochemistry*, 27, 3966–3974, 1988).

The group 3 templates correspond to the same nonfavorable initiation sequence as group 2, followed by the same downstream sequence as group 1.

Results

The results are summarized in the accompanying Table 2.

It is observed that the DNA-RNA transition on the RNA+ 18 template is efficiently passed via the elongation complex, as shown by the absence of an increase in early terminations around position +18, compared with the DNA control.

The T7 RNA polymerase is capable of initiation of transcription on different RNA templates and is capable of fully transcribing these templates. The detection of transcripts having the expected size, for all the groups of templates, shows that the use of the RNA template is not dependent on the sequence, although the overall efficiency depends on the base composition, as is also observed on the control DNA templates.

The different results mentioned in Example 2 above result from the fact that the detection by the Northern blotting technique is in the present case 40 times more sensitive than the detection technique used in Example 2, as was indicated above in the description.

The T7 RNA polymerase is capable of transcribing an RNA-RNA duplex. No increase in the number of abortive products of transcription is observed with the RNA+1 homoduplex template.

The transcription of the homo- or heteroduplex double-stranded templates is similar overall. In the case of the group 2 RNA+18 templates, more transcripts of the expected size are obtained with the homoduplex system than with the heteroduplex system.

The presence of the non-template strand influences the efficiency of transcription. Indeed, the yield of transcription is increased on the single-stranded templates, as shown, on the one hand, by the increase in the number of transcripts of the correct size and, on the other hand, by the fact that an initiation event is more frequently associated with the synthesis of a complete transcript. However, with the group 2 templates, the single-stranded system does not give better results.

Thus, the T7 RNA polymerase possesses transcriptional activity on RNA template, in the presence of a DNA double-stranded promoter. The yield of transcription observed is only 10 to 100 times lower than on DNA template.

TABLE 1

SEQUENCE No. 1:  3' ATTATGCTGAGTGATATCCCTCTAGATCGTCGTATTGCGAGGTTCATGT 5'
                                    +1                  +18

SEQUENCE No. 2:  3' ATTATGCTGAGTGATATCCCAACCGGCGTCACAAGTGAGTACCAATACCG 5'
                                    +1                  +18

SEQUENCE No. 3:  3' ATTATGCTGAGTGATATCCCAACAGATCGTCGTATTGCGAGGTTCATGT 5'
                                    +1                  +18

SEQUENCE No. 4:  3' ATTGCGAGGTTCATGT 5'

SEQUENCE No. 5:  3' GTGAGTACCAATACCG 5'

TABLE 2

| Template | Group (1) | | | Group (2) | | | Group (3) | | |
|---|---|---|---|---|---|---|---|---|---|
| | TS[a] | EI[b] | Eff[c] | TS[a] | EI[b] | Eff[c] | TS[a] | EI[b] | Eff[c] |
| DNA m | 240 | 242 | 1/10 | 192 | 593 | 1/31 | 149 | 633 | 1/43 |
| DNA bho | 80 | 152 | 1/18 | 102 | 191 | 1/19 | 67 | 893 | 1/133 |
| RNA + 18 m | 800 | 650 | 1/8 | 326 | 1488 | 1/45 | 253 | 1246 | 1/49 |
| RNA + 18 bhe | 208 | 309 | 1/14 | 99 | 647 | 1/65 | 61 | 642 | 1/106 |
| RNA + 18 bho | 176 | 272 | 1/16 | 358 | 1093 | 1/31 | nr[e] | nr | nr |
| RNA + 1 m | 13 | 141 | 1/108 | NA[f] | NA | NA | NA[d] | NA | NA |
| RNA + 1 bhe | 3.2 | 61 | 1/227 | NA[d] | NA | NA | NA[d] | NA | NA |
| RNA + 1 bho | 6.4 | 110 | 1/157 | NA[d] | NA | NA | nr | nr | nr |

Comparison of transcription by the T7 polymerase on different templates, by incorporation of $\gamma^{32}$P-GTP
[a]Ts: specific transcript in picomoles per 10 picomoles of template
[b]EI: number of initiation events for one copy of template
[c]Eff: the efficiency corresponds to the number of initiation events leading to the synthesis of a complete transcript
NA: not accessible (nonquantifiable)
d: not accessible; however the complete transcript is detected in Northern blotting
nr: not done

What is claimed is:

1. A method of amplifying an RNA target sequence in an RNA sample comprising said target sequence, said method comprising:

(A) bringing said sample into contact:

with a reagent capable of hybridizing with RNA comprising said target sequence, in the absence of deoxyribonucleoside triphosphates, and with an enzymatic system comprising an RNA polymerase, under conditions allowing the hybridization of said reagent with said RNA comprising said target sequence and under conditions allowing the functioning of said RNA polymerase;

wherein said reagent contains:

(i) a first nucleotide strand comprising: a) a first nucleotide segment capable of playing the role of sense strand of a promoter for said RNA polymerase and b) downstream of said first segment, a second nucleotide segment comprising a sequence capable of hybridizing with a region of said RNA, and (ii) in the hybridized state on the first strand, a second nucleotide strand comprising a third nucleotide segment capable of hybridizing with said first segment so as to form with it a functional double-stranded promoter; and wherein said RNA polymerase (1) is a T7-like phage RNA polymerase and (2) is capable of transcribing an RNA template, in the presence of said reagent hybridized with said template, in the absence of associated protein factor and in the absence of a ligase activity; and (B) amplifying said target sequence by transcription under control of the double-stranded promotor.

2. A method according to claim 1, wherein said third segment is flanked, at its upstream end, by a fourth nucleotide segment which is shorter than said second segment of the first strand.

3. A method according to claim 2, wherein said fourth segment is capable of hybridizing with a portion opposite said second segment.

4. A method according to claim 2, wherein said fourth segment of said second strand is chosen from those whose sequence facilitates the initiation of transcription for said RNA polymerase.

5. A method according to claim 2, wherein said second segment of said first strand contains a number of nucleotides at least equal to the sum of the number of nucleotides of said fourth segment, if it is present, and of the number of nucleotides of said sequence of the second segment which is capable of hybridizing with said region of said RNA.

6. A method according to claim 2, wherein said fourth segment consists of DNA.

7. The method according to claim 2, wherein said fourth segment contains 1 to 18 nucleotides.

8. The method according to claim 7, wherein said fourth segment contains 1 to 12 nucleotides.

9. A method according to claim 1, wherein said first and third segments consist of DNA.

10. A method according to claim 1, wherein said T7-like phage RNA polymerase is selected from the group consisting of T7 RNA polymerase, T3 RNA polymerase and SP6 RNA polymerase.

11. A method according to claim 1, wherein said T7-like phage RNA polymerase is derived by mutation from an RNA polymerase selected from the group consisting of T7, T3 and SP6 RNA polymerases.

12. A method according to claim 11, wherein said RNA polymerase contains at least one mutation in the region corresponding to the T7 RNA polymerase sequence containing amino acids 625 to 652 (SEQ ID NO: 6).

13. A method according to claim 12, wherein said RNA polymerase is capable of transcribing a polynucleotide target sequence with a higher yield when said target sequence consists of RNA than when it consists of DNA.

14. A method according to claim 1, wherein said enzyme system contains only RNA polymerase activity.

15. The method of amplifying an RNA target sequence according to claim 1, wherein promoters of the T7-like phage RNA polymerase have a consensus sequence from position −17 to position −1, relative to position +1 being the site of initiation of transcription.

16. The method according to claim 1, wherein said first segment contains at least 9 nucleotides.

17. The method according to claim 1, wherein said first segment contains at least 6 nucleotides.

* * * * *